United States Patent [19]
Janicki et al.

[11] Patent Number: 5,421,821
[45] Date of Patent: Jun. 6, 1995

[54] VERRES NEEDLE SYSTEM AND METHOD

[75] Inventors: Thomas I. Janicki, Shakerheights; Scott C. Marlow, Chesterland; Haans K. Petruschke, Kirtland; Donald B. Coon, Chesterland, all of Ohio

[73] Assignee: Marlow Surgical Technologies, Inc., Willoughby, Ohio

[21] Appl. No.: 150,956

[22] Filed: Nov. 12, 1993

[51] Int. Cl.⁶ .............................................. A61M 13/00
[52] U.S. Cl. ..................................... 604/26; 128/747; 128/748
[58] Field of Search ............... 604/26, 23, 51, 158, 604/164, 264, 274; 128/747, 748

[56] References Cited

U.S. PATENT DOCUMENTS

| | | | |
|---|---|---|---|
| 3,982,533 | 9/1976 | Wiest | 604/26 |
| 4,356,826 | 11/1982 | Kubota . | |
| 4,464,169 | 8/1984 | Semm | 604/26 |
| 4,869,717 | 9/1989 | Adair | 604/26 X |
| 4,874,362 | 10/1989 | Wiest et al. . | |
| 5,013,294 | 5/1991 | Baier | 604/26 |
| 5,139,478 | 8/1992 | Koninckx et al. . | |
| 5,209,721 | 5/1993 | Wilk . | |

*Primary Examiner*—John D. Yasko
*Attorney, Agent, or Firm*—Thompson, Hine & Flory

[57] ABSTRACT

A verres needle system and method having a tube with an open distal end shaped for insertion through tissue into a body cavity, and a obturator slidably disposed within the tube and being resiliently biased to protrude from the distal end of the tube, and a negative pressure sensor positioned to detect negative pressure at a proximal end of the needle. The negative pressure sensor is connected to a circuit that the sensor closes a switch to eliminate a light when the pressure within the tube in obturator reaches a predetermined value, which indicates that the tip of the needle and obturator are positioned within a body cavity as supposed to body tissue or an organ. The method of utilizing the needle system is to insert the needle into the body cavity while at the same time pulling the tissues surrounding the body cavity away from the cavity to create the negative pressure, which is detected by the pressure sensor and circuit when the tip is properly positioned within the cavity.

18 Claims, 2 Drawing Sheets

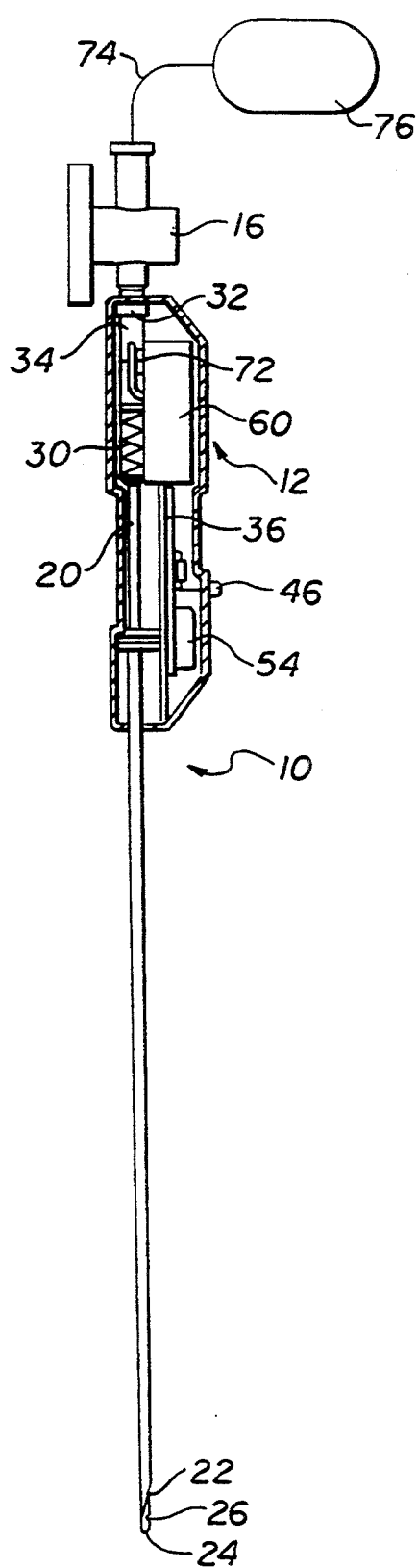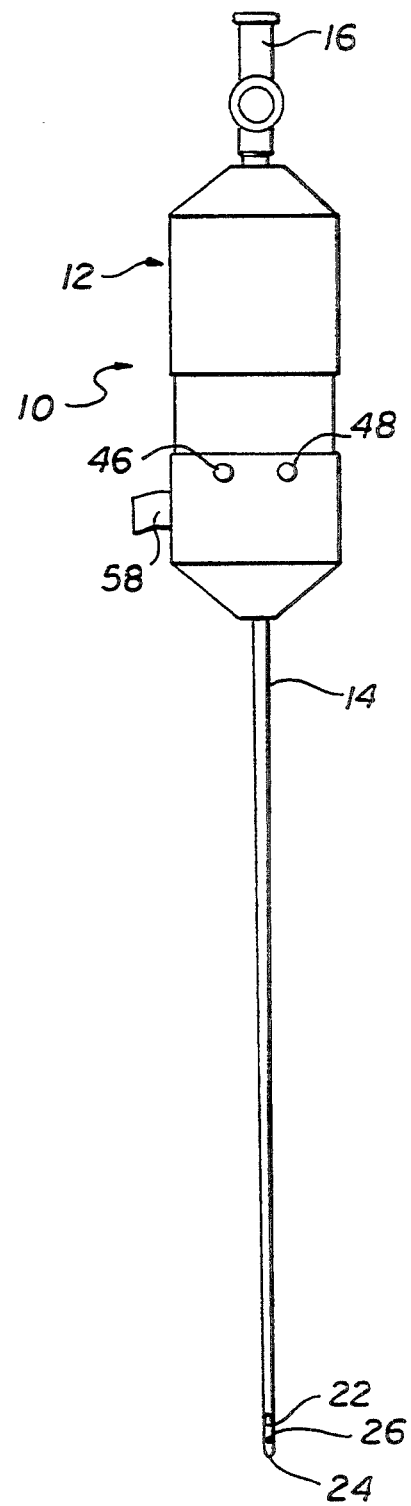
FIG. 1
FIG. 5

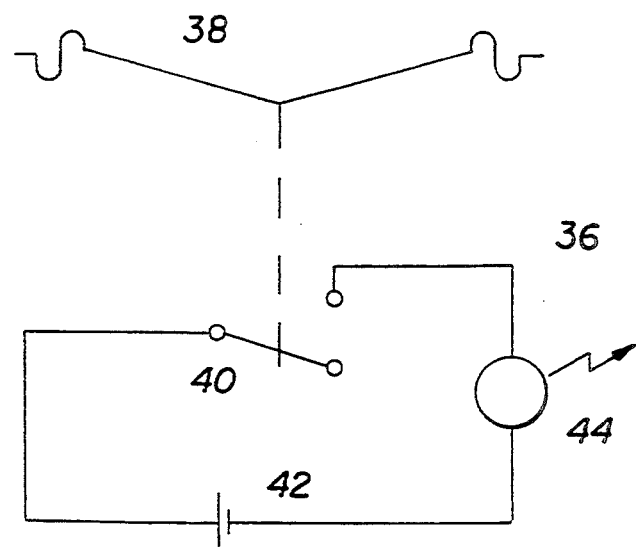
FIG. 2
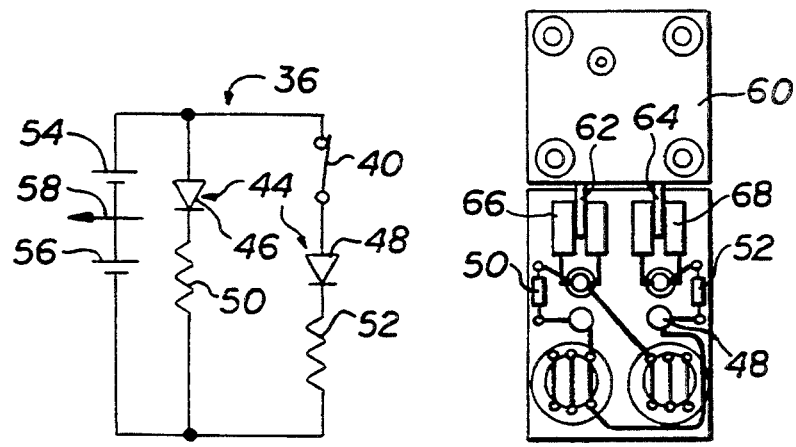
FIG. 3
FIG. 4

VERRES NEEDLE SYSTEM AND METHOD

BACKGROUND OF THE INVENTION

The present invention relates to the instruments for performing endoscopic procedures, and more particularly, for a verres needle system for insufflating a body cavity prior to an endoscopic surgical procedure.

Prior to performing an endoscopic procedure in a body cavity, such as the abdomen, it is first necessary to insufflate the abdominal cavity in order to separate the abdominal wall from the internal organs in the cavity. This separation creates space within which a surgical procedure may be performed by the use of endoscopic instrument, such as laparoscopy instruments in the case of abdominal surgery. The insufflation technique is performed by inserting a verres needle into the abdominal cavity and injecting gas, preferably carbon dioxide gas, through the needle into the cavity to inflate the cavity and thus, separate the abdominal wall from the organs of the cavity. Trocars are then inserted through the abdominal wall which allow laparoscopic instruments to be inserted into the abdominal cavity without allowing the pressurized carbon dioxide gas to escape.

A problem inherent in performing this insufflation technique is that it is currently difficult to determine with a high degree of precision the location of the tip of the verres needle through which gas is injected into the abdomen. It is necessary to position the tip of the needle at a location between the abdominal wall and the organs of the abdominal cavity (or between the tissue wall and the organs of the body cavity, if the technique is being performed in an area other the abdomen).

Should the verres needle tip be positioned inadvertently within the tissue wall surrounding the body cavity, the insufflation procedure could not be performed. Alternately, should the tip of the verres needle be positioned in an organ, artery or the bowel, performing the insufflation technique would result in compressed gas being injected into the organ, artery or bowel, resulting in pain at a minimum, and severe injury or death of the subject at a maximum.

One present device for performing this insufflation technique is a verres needle which includes a hollow tube that slidably receives an obturator within it. The hollow tube has a sharpened, open distal end from which the tip of the obturator protrudes. The obturator itself is a hollow tube having a side opening adjacent its distal end through which compressed gas is injected into the body cavity of the subject. The proximal end of the obturator includes a colored, and large tip which is visible through the clear plastic of the verres needle handle which supports both the obturator and tube. The enlarged tip is displaceable within a chamber within the plastic handle and is spring biased to urge the obturator toward a distal position with respect to the handle.

When such a verres needle is inserted into the subject, the resistance of the tissue wall forces the blunt end of the obturator rearwardly toward the proximal end of the tube, which exposes the sharpened end of the tube to effect its penetration through the tissue wall. Once the distal end of the tube clears the tissue wall, the resistance to further needle penetration caused by the tissue wall is reduced, which allows the spring to urge the obturator forwardly toward the distal end of the tube, resulting in a visibly perceptible displacement of the colored, enlarged end of the obturator within the handle. This displacement indicates that the tip of the needle has cleared the tissue wall surrounding the body cavity.

However, such a displacement could also occur if the needle tip had inadvertently entered the bowel, a soft tissue internal organ, or an artery, resulting in a false indication that the needle tip was properly positioned within the body cavity. Accordingly, there is a need to provide a verres needle system in which the positioning of the needle tip can be determined with a high degree of accuracy. Further, such a verres needle system preferably should be relatively inexpensive, to afford disposability, and simple to use.

SUMMARY OF THE INVENTION

The present invention is a verres needle system and method in which a verres needle can be inserted into a body cavity so that proper positioning of the needle tip within a body cavity for insufflation can be effected with a high degree of accuracy. The verres needle system includes a verres needle tube and obturator which are attached to a housing that also encloses a negative pressure sensing diaphragm switch. The diaphragm switch is connected to an electric circuit such that, upon detecting a negative pressure of a predetermined threshold value, a circuit is made in which an indicator light is illuminated, thereby indicating to the user the presence of the negative pressure and the proper positioning of the needle tip within the body cavity.

To perform the method of the invention, the verres needle is inserted through the tissue wall of the subject, and at the same time the tissue wall is pulled away from the organs of the body cavity which it surrounds. This pulling of the tissue wall creates a negative pressure within the body cavity. Once the tip of the needle has cleared the tissue wall and entered the body cavity, the negative pressure within the body cavity caused by the tissue displacement results in a lowered pressure within the housing. This negative pressure causes the pressure switch to close, thereby making a circuit and illuminating the indicator light.

If the needle tip of the verres needle system of the present invention is inadvertently inserted into a body organ, the bowel or an artery, the displacement of tissue away from the organs of the body cavity will not affect the pressure within the housing since such manual tissue displacement does not have an effect on the internal pressure of such body parts as the bowel, internal organs and arteries. Accordingly, the relative pressure within the housing will not drop to the point where the contact switch is closed and the light illuminated. Accordingly, under such circumstances, the user of the verres needle system of the present invention will realize that the tip of the verres needle is not properly positioned within the body cavity, since the indicator light will not be illuminated.

In the preferred embodiment of the invention, the circuit containing the indicator light also includes a second indicator light, of a different color, which is illuminated when the circuit is activated. This way, a user will be told at a glance that the system is energized and that the absence of the first indicator light illumination is due to the positioning of the needle tip and not to a power failure or other mechanical or electrical defect in the system.

Also in the preferred embodiment, the housing is shaped to receive a stopcock which communicates with the obturator so that the verres needle system, once properly positioned within a body cavity, may be connected to a source of gas, such as carbon dioxide gas, under pressure. Consequently, the opening of the stopcock connected in that manner will permit an insufflation of the body cavity to occur.

Accordingly, it is an object to the present invention to provide a verres needle system and method in which the proper positioning of the verres needle tip within a body cavity can be determined with a high degree of precision; a verres needle system and method in which verres needle indicator lights, pressure detector mechanism and power supply are conveniently contained within a unitary, hand-held housing; a verres needle system which can be operated with one hand, allowing the other hand of the user to perform a tissue separating movement; a verres needle system and method which is relatively easy to use; and a verres needle system and method in which the verres needle system is sufficiently inexpensive to manufacture to allow single-use operation.

Other objects and advantages of the present invention will be apparent from the following description, the accompanying drawings and appended claims.

BRIEF DESCRIPTION OF THE DRAWINGS

FIG. 1 is a side elevation in section of a preferred embodiment of the verres needle system of the present invention;

FIG. 2 is a schematic diagram showing the pressure switch and circuit of the embodiment of FIG. 1;

FIG. 3 is a detailed electric schematic of the embodiment of FIG. 1;

FIG. 4 is a diagram of the circuit of FIG. 3; and

FIG. 5 is a front elevation view of the embodiment of FIG. 1.

DETAILED DESCRIPTION

As shown in FIG. 1, the verres needle system the present invention, generally designated 10, includes a housing 12 which supports a needle or tube 14 and a stopcock 16. The needle 14 has a pointed, open distal end 18 and proximal end 20 which is retained within the housing 12. An obturator 22 is slidably mounted within the needle 14 and includes a blunt distal end 24 having a side opening 26, and a proximal end which terminates in an enlarged end 28 within the housing 12.

The obturator 22 is hollow along its length so that the side opening 26 communicates with the interior of the housing 12. A spring 30 is mounted within the housing and is oriented to bias the obturator outwardly from the housing towards the distal end 18 of the needle 14. The head 28 of the obturator and the nipple 32 of the stopcock 16 are interconnected by a manifold 34 retained within the housing 12.

Pressure within the manifold 34 is detected by a pressure sensing mechanism, generally designated 36. As shown FIGS. 2 and 3, the pressure sensing mechanism 36 includes a negative pressure sensing diaphragm 38 (see FIG. 2) which is connected to a mechanical switch 40. The switch 40 is connected to a battery unit 42 and a light array 44.

As shown in FIG. 3, the light array 44 includes yellow and green light emitting diodes 46, 48, respectively, in series with resistors 50, 52, respectively. As shown in FIG. 3, the battery unit 42 comprises a pair of battery elements 54, 56 activated by a pull strip 58 (see also FIG. 5).

As shown in FIGS. 2 and 4, the diaphragm 38 and switch 40 (see FIG. 2) preferably are combined in a pressure switch 60 mounted within the housing and include contacts 62, 64 which engage clip pairs 66, 68 respectively, connected on a circuit board 70 to resistors 50, 52. The pressure switch 60 is of conventional design, such as the pressure sensor manufactured by World Magnetics of Traverse City, Mich. Pressure switch 60 includes an orifice 72 which communicates with the manifold 34 (see FIG. 1). Consequently, changes in pressure within manifold 34 with respect to ambient pressure activate switch 60 to open or close the circuit shown in FIG. 3. In the preferred embodiment, a negative pressure relative to ambient in the order of one-half inch of water or greater is sufficient to close the switch 40 to illuminate the green diode 48.

The stopcock 16 is also a conventional design and receives a flexible tube 74 that is connected to a source gas 76 under pressure, preferably carbon dioxide gas.

The operation of the verres needle system 10 is as follows. Initially, the pull tab 58 is removed from the housing 12, which allows the batteries 54, 56 to energize the circuit 36. This activation of the system 10 is indicated to a user by the steady illumination of yellow diode 46. The housing 12 is then grasped by the user and the needle 14 is placed against the abdominal wall of the subject. The tip 18 of the needle is inserted through the abdominal wall, and simultaneously, the abdominal wall is grasped by the user and pulled outwardly from the organs in the body cavity surrounded by the abdominal wall. This pulling action creates a negative pressure within the abdominal cavity.

As the needle penetrates the abdominal wall, the resistance created by the abdominal wall urges the obturator 22 towards the proximal end 20 of the needle 14, which compresses the spring 30. During this step of the process, the pressure within the manifold 34 remains relatively constant, so that the switch 60 does not close the circuit 36.

Once the needle tip 18 clears the abdominal wall, the pressure and resistance which have displaced the obturator 22 no longer exist, allowing the spring 32 urge the obturator 22 toward the distal end 18 of the needle 14. Consequently, the negative pressure within the abdominal cavity is communicated through the hollow obturator 22 to the manifold 34 where the pressure differential between the manifold pressure and ambient is detected by the pressure switch 60. Once this pressure differential reaches one-half inch of water, the switch 40 (see FIGS. 2 and 3) is closed, thereby energizing green diode 48.

At this time, the flexible tube 74 is connected to the stopcock 16, which has, up to now, been in a closed configuration. The stopcock 16 is opened, and pressurized gas from source 76 allow to-flow through the stopcock 16, manifold 34 and obturator 22, and into the body cavity. The rounded tip 24 of the obturator projects beyond the pointed distal end 18 of the needle 14, thereby protecting internal organs, arterial walls and the like from being damaged by the tip 18 during the insufflation process.

Should the needle 14 inadvertently enter the bowel, an artery or internal organ, the negative pressure created by pulling away of the abdominal wall would not be felt within such organs, and therefore the threshold negative pressure of one-half inch of water would not exist within the manifold 34. Accordingly, the switch 40 is not closed and the green diode 48 is not illuminated.

This signals the user that the needle tip 18 is not properly positioned within the body cavity. Once the insufflation technique has been performed and the needle 14 removed from the subject, the verres needle system 10 may be disposed of.

In preferred embodiment, the needle and obturator 14, 22 preferably are made of a surgical stainless steel, and the housing 12 preferably made of ABS plastic. The manifold 34 and pressure switch 60 preferably are made of polycarbonate.

While the forms of apparatus disclosed herein constitute preferred embodiments of the invention, it is to be understood that the invention is not limited to these precise forms of apparatus, and that changes may be made therein without departing from the scope of the invention.

What is claimed is:

1. A verres needle system comprising:
    means forming a tube having an open distal end shaped for insertion through tissue into a body cavity;
    means forming an obturator slidably disposed within said tube means, said obturator means having an open distal end and being resiliently biased to protrude from said distal end of said tube means, thereby exposing said open distal end of said obturator means, said obturator means being displaceable toward a proximal end of said tube means whereby said tube means open end is exposed;
    means forming a housing integral with said tube means and said obturator means and shaped to be grasped and held by a user during use of said system, said housing means enclosing
        means, positioned adjacent to said proximal end of said obturator means, for detecting negative pressure in said obturator means at a distal end thereof prior to insufflation; and
        indicating means which is activated upon said detected negative pressure, whereby a user is informed that said tube means open end is properly positioned within a body cavity.

2. The system of claim 1 further comprising means for supplying a gas under pressure to a proximal end of said obturator means, whereby said gas is conveyed along said obturator means to exit said distal end thereof when said obturator means open end is exposed in said body cavity.

3. The system of claim 1 wherein said detecting means includes a pressure switch.

4. The system of claim 3 wherein said pressure switch includes a negative pressure sensing diaphragm.

5. The system of claim 1 wherein said indicating means includes visual means for indicating said pressure change.

6. The system of claim 5 wherein said visual means includes a first light emitting diode.

7. The system of claim 6 wherein said indicating means includes means for providing electrical energy, said detecting means being in series with said diode and said electrical energy providing means.

8. The system of claim 7 wherein said visual means includes a second light emitting diode, said second diode being connected in parallel with said first diode and said detecting means, said first diode indicating that electrical energy is being supplied to said first diode.

9. The system of claim 8 wherein said indicating means includes pull strip means for activating and deactivating said electromotive force providing means, thereby activating and deactivating said readout means.

10. The system of claim 1 further comprising valve means for pressurizing and depressurizing said obturator means with said gas.

11. The system of claim 1 further comprising means forming a housing for supporting said tube means and said obturator means, said housing including a manifold communicating with said obturator proximal end and said detecting means, whereby said detecting means detects gas pressure within said manifold, said gas pressure corresponding to gas pressure at said obturator open distal end.

12. The system of claim 11 wherein said housing is shaped to enclose said detecting means and said readout means.

13. A verres needle system comprising:
    means forming a tube having an open distal end shaped for insertion through tissue into a body cavity;
    means forming an obturator slidably disposed within said tube means, said obturator means having an open distal end and being resiliently biased to protrude from said distal end of said tube means, thereby exposing said open distal end of said obturator means, said obturator means being displaceable toward a proximal end of said tube means whereby said tube means open end is exposed;
    means forming a housing shaped to receive said proximal end of said tube means, said housing means including manifold means communicating with said obturator means;
    means, positioned within said housing means and communicating with said manifold means, for detecting a negative pressure in said obturator means and said manifold means; and
    indicating means which is activated upon said detected negative pressure, whereby a user of said system is informed that said tube means open end is properly positioned within a body cavity.

14. A method for preparing an abdominal cavity for an endoscopic procedure, said method comprising the steps of:
    inserting tube means having an open distal end through tissue into a body cavity, and simultaneously pulling an associated body cavity side wall away from said cavity, thereby creating a negative pressure within said cavity;
    providing obturator means slidably disposed within said tube means, said obturator means having an open distal end and being resiliently biased to protrude from said distal end of said tube means, thereby exposing said open distal end of said obturator means, when in said cavity, said obturator means being displaceable toward a proximal end of said tube means when in contact with tissue surrounding said cavity, thereby exposing said end of said tube means;
    detecting a change in pressure in said obturator means at said proximal end of said obturator means resulting from said distal end of said obturator means being positioned within said body cavity having negative pressure; and
    indicating means which is activated upon said detected negative pressure, whereby a user is informed that said tube means open end is properly positioned within said cavity prior to performing insufflation.

15. The method of claim 14 further comprising the step of insufflating said cavity of said patient with gas under pressure, said gas being conveyed through said tube means.

16. The method of claim 14 wherein said readout providing step includes the step of illuminating a light emitting diode.

17. The method of claim 14 further comprising the step of supplying a gas under pressure to a proximal end of said obturator means, whereby said gas is conveyed along said obturator means to exit said distal end thereof, when said obturator means open end is exposed, thereby insufflating said body cavity.

18. The system of claim 1 wherein said distal end of said obturator means is received within said housing.

* * * * *